(12) United States Patent
Stern et al.

(10) Patent No.: US 8,784,389 B2
(45) Date of Patent: Jul. 22, 2014

(54) OXYGEN SUPPLY FOR IMPLANTABLE MEDICAL DEVICE

(75) Inventors: Jacob Stern, Shoham (IL); Avi Rotem, Petach-Tikva (IL); Yoav Hevron, Hod Hasharon (IL); Yehezkel Bermer, Raanana (IL)

(73) Assignee: Beta-O2 Technologies Ltd., Kiryat Aryeh (IL)

( * ) Notice: Subject to any disclaimer, the term of this patent is extended or adjusted under 35 U.S.C. 154(b) by 1332 days.

(21) Appl. No.: 12/551,151

(22) Filed: Aug. 31, 2009

(65) Prior Publication Data
US 2011/0054387 A1     Mar. 3, 2011

(51) Int. Cl.
*A61M 37/00* (2006.01)

(52) U.S. Cl.
USPC .................... 604/288.01; 604/23; 604/502

(58) Field of Classification Search
CPC ............... A61M 2005/006; A61M 2039/0211; A61M 2039/0217; A61M 2202/0208; A61M 2209/045; A61M 39/0208; A61M 5/1582
USPC ............. 604/22–24, 26, 288.01–288.04, 500, 604/502–507, 890.1; 424/423
See application file for complete search history.

(56) References Cited

U.S. PATENT DOCUMENTS

| | | | | |
|---|---|---|---|---|
| 2,564,977 | A | * | 8/1951 | Hu .................................. 604/32 |
| 5,262,055 | A | * | 11/1993 | Bae et al. ....................... 210/645 |
| 2005/0136092 | A1 | * | 6/2005 | Rotem et al. ................... 424/423 |
| 2007/0233019 | A1 | * | 10/2007 | Forsell ...................... 604/288.03 |
| 2008/0294096 | A1 | * | 11/2008 | Uber et al. ........................ 604/66 |

* cited by examiner

*Primary Examiner* — Kami A Bosworth
*Assistant Examiner* — Imani Hayman
(74) *Attorney, Agent, or Firm* — Browdy and Neimark, PLLC

(57) ABSTRACT

A method for replenishing gas in a subcutaneously implanted medical device containing functional cells comprising: inserting at least one needle, adopted to penetrate the skin and connecting a subcutaneously implanted medical device; connecting the inserted at least one needle to a gas replenishing apparatus; extracting gas from a gas reservoir in the implanted device into the gas replenishing apparatus; sensing oxygen level in the extracted gas; calculating the amount of gas needed for replenishing oxygen in the reservoir based on the sensed oxygen level in the extracted gas; and supplying gas from a gas tank in the gas replenishing apparatus to the gas reservoir in the implanted device.

34 Claims, 16 Drawing Sheets

(i)

(ii)

OXYGEN SUPPLY FOR IMPLANTABLE MEDICAL DEVICE

FIELD OF THE INVENTION

The present invention relates generally to an implantable medical devices and to an apparatus and method for providing oxygen to the transplanted cells, e.g., cells in transplanted pancreatic islets within said implanted medical device.

BACKGROUND OF THE INVENTION

Oxygen is vital to all physiological processes. An insufficient supply of oxygen to implanted cells often leads to cell injury or death. Oxygen provision is a vital component in sustaining transplanted cells.

In healthy individuals, insulin release is regulated so as to maintain blood glucose levels in the range of about 70 to 110 milligrams per deciliter. In diabetics, insulin is either not produced at all (Type I diabetes), or the body cells do not properly respond to the insulin that is produced (Type II diabetes). The result is elevated blood glucose levels.

The success of many cellular transplants is compromised not only due to graft-host rejections, but also on account of ischemic conditions generated by insufficient oxygen supply to the transplant. Following implantation of the cells, oxygen is provided to the implanted cells from the body tissue (mainly via diffusion), and in some cases, from vascular structures that form around the transplanted cells with the help of angiogenic factors, e.g., VEGF and bFGF. However, the natural diffusion rate is too low to provide the cells with a significant, necessary amount of oxygen.

PCT Publication WO 01/50983 titled "IMPLANTABLE DEVICE"; to Vardi et al., and U.S. patent application Ser. No. 10/466,069 in the national phase thereof, which are incorporated herein by reference, describe an implantable device comprising a chamber for holding functional cells and an oxygen generator for providing oxygen to the functional cells.

In one embodiment, the oxygen generator is described as comprising photosynthetic cells that convert carbon dioxide to oxygen when illuminated. In another embodiment, the oxygen generator is described as comprising electrodes that produce oxygen by electrolysis.

US Patent Application Publication 2005/0136092 to Rotem, which is incorporated herein by reference, describes apparatus including a chamber, which is adapted to be implanted in a body of an individual, the chamber including functional cells and chlorophyll-containing elements comprising chlorophyll of an obligate photoautotroph. Typically, the chlorophyll-containing elements include intact photosynthetic cells and/or isolated chloroplasts. The chlorophyll-containing elements provide oxygen to the functional cells and/or consume carbon dioxide produced by the functional cells.

The chamber has one or more walls that are adapted to be permeable to nutrients and substances produced or secreted by the cells. The walls also typically immunoisolate the cells from constituents of the body. The chamber is adapted to be implanted under skin of the subject, or in the peritoneum. The apparatus further comprises a light source that is adapted to provide light to the chlorophyll-containing elements. The chamber may comprise an oxygen sensor that detects an oxygen concentration in vicinity of the functional cells, and/or in a vicinity of the chlorophyll-containing elements. Providing the light in the series of pulses generally reduces power consumption of the apparatus, and/or provides control of the quantity of oxygen produced by the chlorophyll-containing elements, and/or provides control of the quantity of carbon dioxide consumed by the chlorophyll-containing elements. In some embodiments of the invention, the chamber comprises an oxygen reservoir, which typically comprises a material that stores and releases oxygen, such as responsively to an oxygen concentration in a vicinity of the reservoir.

The oxygen reservoir typically stores oxygen produced by the chlorophyll-containing elements that is in excess of the current needs of the functional cells, and releases the stored oxygen if insufficient oxygen is later generated by the chlorophyll-containing elements.

PCT Publication WO 06/059322 to Evron et al., describes apparatus including a chamber which is adapted to be implanted in a body of an individual. The chamber includes functional cells and chlorophyll-containing elements comprising chlorophyll of an obligate photoautotroph. Other embodiments are also described.

U.S. Pat. No. 5,713,888 to Neuenfeldt et al., describes an implant assembly for a host tissue. The implant assembly comprises a pouch including wall means defining a chamber for holding a second member. The wall means includes an outer vascularizing membrane having a conformation that results in growth of vascular structures by the host tissue, close to an interface between the vascularizing membrane and host tissue. The assembly includes a second member that can be removably inserted in the chamber including an interior for receiving cells and wall means defining an immunoisolating membrane that isolates the cells from the immune response of the host tissue.

U.S. Pat. No. 6,368,592 to Colton et al., describes techniques for supplying oxygen to cells in vitro or in vivo by generating oxygen with an oxygen generator that electrolyzes water to oxygen and hydrogen.

U.S. Pat. No. 6,960,351 to Dionne et al., describes an immunoisolatory vehicle for the implantation into an individual of cells which produce a needed product or provide a needed metabolic function. The vehicle is comprised of a core region containing isolated cells and materials sufficient to maintain the cells, and a permselective, biocompatible, peripheral region free of the isolated cells, which immunoisolates the core yet provides for the delivery of the secreted product or metabolic function to the individual. The vehicle is described as being particularly well-suited to delivery of insulin from immunoisolated islets of Langerhans, and as being used advantageously for delivery of high molecular weight products, such as products larger than Immunoglobulin G (IgG).

US application 20090012502A1; titled "Oxygen Supply for Cell Transplant and Vascularization"; to Rotem Avi, et. al. describes an apparatus including a housing configured for insertion into a body of a patient; a photosynthetic oxygen supply configured to supply oxygen; and functional cells, coupled to the housing. The functional cells are adapted to receive the oxygen and to secrete at least one factor that induces vascularization in a vicinity of the housing when the housing is in the body of the patient. Other embodiments are also described.

PCT publication WO2009031154; titled "Air Gap For Supporting Cells"; to Stern Yaki, et. al. discloses an implantable medical device for transplanting functional pancreatic islet cells into subject for producing insulin, and providing oxygen to said transplanted cells. The device has housing comprising photosynthetic oxygen supplies and cells, and gas.

PCT publication WO2008062417; titled "Protecting Algae from Body Fluids", to Rotem Avi, et. al. describes an apparatus for implantation into body of subject and providing oxygen to cells. The apparatus has isolated functional cells, photosynthetic elements, and semi-permeable barriers for protecting cells and elements from body fluid components.

U.S. Pat. No. 5,013,298; titled "Laterally compressed septum assembly and implantable infusion port with laterally compressed septum"; to Moden James, et. al. discloses a septum assembly port with elastomeric septum which can be penetrated by hypodermic needle.

The paper titled "High strength porous Ti-6A1-4V foams synthesized by solid state powder processing"; to Min Ha Lee, et. al; published in J. Phys. D: Appl. Phys. 41 (2008) 105404 (5pp); discloses production and high strength porous metal structures.

The following patents and patent applications may be of interest:

PCT Publication WO 07/138590 to Gross
U.S. Pat. No. 2,564,977 to Hu
U.S. Pat. No. 4,721,677 to Clark, Jr. et al.
U.S. Pat. No. 5,614,378 to Yang et al.
U.S. Pat. No. 6,268,161 to Han, et al.
U.S. Pat. No. 6,383,478 to Prokop, et al.
U.S. Pat. No. 6,630,154 to Fraker, et al.
US Patent Application Publication 2003/0113302 to Revazova et al.
US Patent Application Publication 2005/0025680 to Monzyk et al.
US Patent Application Publication 2006/0024276 to Ricordi et al.

The following articles may be of interest:

Kaisers U et al., "Liquid ventilation," British Journal of Anaesthesia 91(1):143-151 (2003)

Lacy P E et al., "Maintenance of normoglycemia in diabetic mice by subcutaneous xenografts of encapsulated islets," Science 1782-4 (1991)

Lorch H et al., "Central Venous Access Ports Placed by Interventional Radiologists: Experience with 125 Consecutive Patients," Journal CardioVascular and Interventional Radiology, Pages 180-184, Issue Volume 24, Number 3 (2001)

Silva A I et al., "An overview on the development of a bio-artificial pancreas as a treatment of insulin-dependent diabetes mellitus," Med Res Rev 26(2):181-222 (2006)

Waschke K F and Frietsch T, "Modified haemoglobins and perfluorocarbons" (Current Opinion in Anaesthesiology. 12(2):195-202 (1999)

SUMMARY OF THE INVENTION

The present invention relates generally to an implantable medical device and to an apparatus and method for providing oxygen or other gases to the transplanted cells, e.g., cells in transplanted pancreatic islets within said implanted medical device.

According to the current invention, an implantable medical device is provided.

In some embodiments of the present invention, the implanted medical device comprises a housing for containing transplanted functional cells that is designated for subcutaneous implantation into the body of a subject. The transplanted cells typically comprise functional cells, e.g., cells disposed in pancreatic islet of Langerhans cells, and in this case are typically in islets. The functional cells are typically disposed in a layer of gel. Optionally, the functional cells are adapted to secrete at least one factor that induces vascularization in a vicinity of the housing when the housing is in the body of the patient.

Typically, the housing comprises an oxygen reservoir, which functions as a conduit for oxygen diffusion as well as a reservoir for storing excess oxygen that is supplied to the housing by the oxygen replenishing apparatus. In some embodiments, the oxygen reservoir comprises a gas reservoir. Gas in the gas reservoir may comprise oxygen, and carbon dioxide and water vapor. Optionally, Gas in the gas reservoir may comprise also nitrogen or other inert gas. Optionally the Gas mixture in the gas reservoir comprises around 5% carbon dioxide in order to maintain a balance of concentrations of carbon dioxide inside the housing and outside the housing. Optionally percentage of oxygen in the gas mixture is similar or higher than atmospheric percentage of oxygen.

The implant implanted medical device may further comprise at least one subcutaneous oxygen replenishing port. Oxygen level in the gas reservoir is maintained by periodically interfacing the subcutaneous oxygen replenishing port with an oxygen replenishing apparatus via at least one hollow needle connected to said oxygen replenishing apparatus. The needle penetrates the skin and enters the subcutaneous oxygen replenishing port. Oxygen is than pumped into the gas reservoir to replenish the oxygen consumed by the functional cells. Optionally, at least some of the gas in the gas reservoir is replaced or vent during the oxygen replenishing process.

Typically, oxygen is supplied to the housing in a volume and concentration in accordance with the size of the housing and with the number of functional cells disposed therein. Additionally, the amount of oxygen delivered to the housing depends on the composition of the oxygen carriers injected into the housing. In general, the oxygen delivery interface facilitates the provision, on a consistent basis, of oxygen to the functional cells in a volume and concentration sufficient to meet the oxygen consumption rate of the functional cells over a given period of time, e.g., between 12 hours and 2 weeks. The present invention relates to According to an exemplary embodiment of the invention, a gas replenishing apparatus for replenishing gas in a subcutaneously implanted medical device containing functional cells is provided, the apparatus comprising: at least one needle, adopted to penetrate the skin and connect to a subcutaneously implanted medical device; a gas tank holding gas for replenishing gas in said implanted device; a gas handling sub-system, adopted for supplying gas from said gas tank into said a gas reservoir in said implanted device; at least one gas sensor selected from: an oxygen sensor sensing oxygen level in gas extracted from said reservoir; and pressure transducer measuring pressure in said reservoir; and a processor, controlling said gas handling sub-system in response to reading of said at least one of said oxygen sensor and said pressure transducer.

In some embodiments the apparatus further comprises least one hose connecting said needle to said replenishing apparatus. In some embodiments the hose is flexible. In some embodiments the gas handling sub-system is adopted for extracting gas from said gas reservoir; and said processor, controls said gas handling sub-system in response to sensed oxygen level in said extracted gas. In some embodiments the gas in said gas tank comprises oxygen. In some embodiments the gas in said gas tank comprises at least 30% oxygen. In some embodiments the gas in said gas tank comprises at least 50% oxygen. In some embodiments the said gas in said gas tank further comprises at least one gas selected from a group comprising: Nitrogen, Carbon dioxide; water vapor and noble gas. In some embodiments the gas handling sub-system comprises a gas pump for extracting gas from said gas reservoir. In some embodiments the apparatus further comprises an output valve, controlled by said processor for controlling amount of gas supplied from said gas tank into said reservoir. In some embodiments the gas sensor is a pressure transducer; and said processor, controls said gas handling sub-system in response to sensed pressure in said gas reservoir. In some embodiments the apparatus comprises at least one pressure transducer monitoring gas pressure within said gas handling sub-system. In some embodiments the at least one needle, adopted to penetrate the skin and connect to a subcutaneously implanted medical device is a single needle used for both extracting gas from a gas reservoir in said implanted device and supplying gas from said gas tank into said reservoir. In some embodiments the at least one needle, adopted to penetrate the skin and connect to a subcutaneously implanted medical device is a single needle having a first and a second channel, wherein said first channel is used for extracting gas from said gas reservoir, and said second channel is used for supplying gas from said gas tank into said reservoir. In some embodiments the channels in said dual-channeled single needle are coaxial. In some embodiments the at least one needle, comprises a first and a second needle, wherein said first needle is used for extracting gas from said gas reservoir, and said second needle is used for supplying gas from said gas tank into said reservoir. In some embodiments the first needle and a second needle are inserted into a first and a second gas ports of said implanted device respectively. In some embodiments the at least one needle is adopted to penetrate a gas port which is an integral part of said implanted device. In some embodiments the at least one needle is adopted to penetrate a gas port which is connected to said implanted device via a flexible tube.

According to an exemplary embodiment of the invention, a method for replenishing gas in a subcutaneously implanted medical device containing functional cells is provided, the method comprising: inserting at least one needle, adopted to penetrate the skin and connecting to a subcutaneously implanted medical device; connecting said inserted at least one needle to a gas replenishing apparatus; extracting gas from a gas reservoir in said implanted device into said gas replenishing apparatus; sensing oxygen level in said extracted gas; calculating the amount of gas needed for replenishing oxygen in said reservoir based on said sensed oxygen level in said extracted gas; and supplying gas from a gas tank in said gas replenishing apparatus to said gas reservoir in said implanted device.

In some embodiments the gas in said gas tank comprises at least one gas selected from a group comprising: Oxygen, Nitrogen, Carbon dioxide; water vapor and noble gas. In some embodiments the step of extracting gas from said gas reservoir comprises pumping said extracted gas. In some embodiments the step of supplying gas from a gas tank in said gas replenishing apparatus to said gas reservoir in said implanted device comprising opening an output valve, controlled by a processor. In some embodiments the step of supplying gas from a gas tank in said gas replenishing apparatus to said gas reservoir in said implanted device comprising operating a gas compressor controlled by a processor. In some embodiments the step of supplying gas from a gas tank in said gas replenishing apparatus to said gas reservoir in said implanted device comprising reducing gas pressure of gas in said tank by a pressure regulator. In some embodiments the step of inserting at least one needle, adopted to penetrate the skin and connect to a subcutaneously implanted medical device comprises inserting a single needle used for both extracting gas from a gas reservoir in said implanted device and supplying gas from said gas tank into said reservoir. In some embodiments the step of inserting at least one needle, adopted to penetrate the skin and connect to a subcutaneously implanted medical device comprises inserting a single needle having a first and a second channel, wherein said first channel is used for extracting gas from said gas reservoir, and said second channel is used for supplying gas from said gas tank into said reservoir. In some embodiments the step of inserting at least one needle, adopted to penetrate the skin and connect to a subcutaneously implanted medical device comprises inserting a first and a second needle into a first and a second gas ports of said implanted device respectively, wherein said first needle is used for extracting gas from said gas reservoir, and said second needle is used for supplying gas from said gas tank into said reservoir. In some embodiments the at least one needle is adopted to penetrate a gas port which is an integral part of said implanted device. In some embodiments the at least one needle is adopted to penetrate a gas port which is connected to said implanted device via a flexible tube.

According to another exemplary embodiment of the invention, a method for replenishing gas in a subcutaneously implanted medical device containing functional cells is provided, the method comprising: inserting at least one needle, adopted to penetrate the skin and connecting to a subcutaneously implanted medical device; connecting said inserted at least one needle to a gas replenishing apparatus; measuring the gas pressure in a reservoir in said implanted device; calculating the amount of gas needed for replenishing oxygen in said reservoir based on said sensed pressure in said extracted gas; and supplying gas from a gas tank in said gas replenishing apparatus to said gas reservoir in said implanted device.

According to an exemplary embodiment of the invention, a system for maintaining functional cells in implanted medical device is provided, the system comprising: an implanted medical device, implanted within a patient's body, the implanted device comprising: a gas reservoir; a gel layer disposed with a plurality of functional cells, and protected from the boy immune system by a first membrane, and receiving oxygen from said gas reservoir; and at least one gas port located subcutaneously and adopted to receive replenishing gas supply from a gas replenishing apparatus located outside said patient's body; and gas replenishing apparatus for replenishing gas in a said implanted medical device, said apparatus comprising: at least one needle, adopted to penetrate the skin and connect to said implanted medical device; at least one flexible hose, connecting said needle to said replenishing apparatus; a gas tank holding gas for replenishing gas in said implanted device; a gas handling sub-system, adopted for extracting gas from a gas reservoir in said implanted device and supplying gas from said gas tank into said reservoir; an oxygen sensor, sensing oxygen level in said extracted gas; and a processor, controlling said gas handling sub-system in response to said sensed oxygen level in said extracted gas.

In some embodiments the implanted device comprises at least a first and a second gas ports, both connected to said gas reservoir. In some embodiments the gas replenishing apparatus comprises a first and a second needle inserted into said first and a second gas ports of said implanted device respectively, wherein said first needle is used for extracting gas from said gas reservoir, and said second needle is used for supplying gas from said gas tank into said reservoir. In some embodiments the implanted device further comprises a buffer gas chamber locating between said gel layer with functional cells, and separated from said by gas reservoir by a second membrane. In some embodiments the implanted device comprises at least a first and a second gas port, wherein said first gas port is connected to said gas reservoir, and said second port is connected to said buffer gas chamber. In some embodiments the gas replenishing apparatus comprises at least a first and a second needle inserted into said first and a second gas ports of said implanted device respectively, wherein said first needle is used for extracting gas from said buffer gas chamber, and said second needle is used for supplying gas from said gas tank into said gas reservoir.

According to another aspect of the current invention, a simplified gas replenishing apparatus for replenishing gas in a subcutaneously implanted medical device containing functional cells is provided the simplified apparatus comprising: at least one needle, adopted to penetrate the skin and connect to a subcutaneously implanted medical device; a gas tank holding gas for replenishing gas in said implanted device; a gas handling sub-system, adopted for supplying a predetermined amount of gas from said gas tank into said a gas reservoir in said implanted device.

In this simplified apparatus, the gas sensors may be missing. Optionally a gas pressure relief valve may be used to prevent over pressure in the implanted device, optional tubes or hoses. The predetermined volume of gas may be selected by timing the opening of the gas valves. Alternatively, a gas chamber fitted with a piston may be filled with gas at elevated pressure and than used. Alternatively, a piston fitted chamber (syringe) may be filled with gas and emptied into the implanted device by pushing the syringe manually or using an actuator such an electrical motor.

Similarly, the processor may be missing in this simplify embodiment. In these cases, user interface may be simplified, missing or purely mechanical. For example, user interface may comprise one or few of: mechanical gas pressure measuring the gas in the gas tank only, a timer (mechanical or electronic), gas handling valve actuators, etc.

In these embodiments, spent gas may be vented directly to the room, optionally through a HEPA filter to avoid contamination of the room or the implanted device.

In some embodiments the simplified apparatus further comprising a timer, wherein said timer is adopted to measure the time elapsed since last gas replenishing, and wherein said predetermined amount of gas is selected according to said elapsed time.

In some embodiments the predetermined amount of gas is fixed and wherein time between consecutive gas replenishing is substantially fixed.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts. The drawings are generally not to scale. For clarity, non-essential elements were omitted from some of the drawings. Some optional parts were drawn using dashed lines.

In the drawings:

Figure 1:
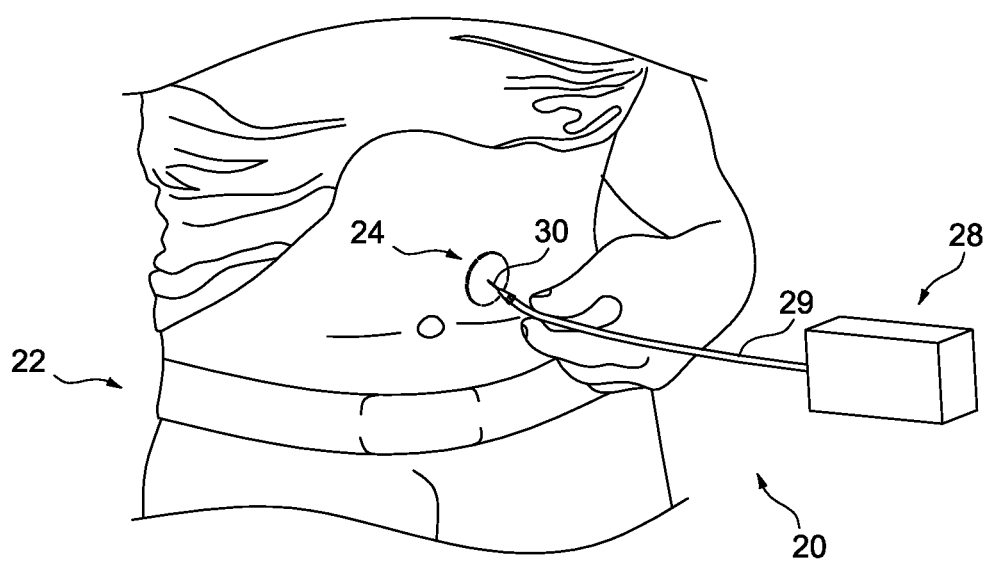

FIG. 1 schematically depicts a medical system according to an exemplary embodiment of the current invention.

FIG. 2($a$) schematically depicts an implantable medical device according to an exemplary embodiment of the current invention.

FIG. 2($b$) schematically depicts an implantable medical device according to another exemplary embodiment of the current invention.

Figure 3:
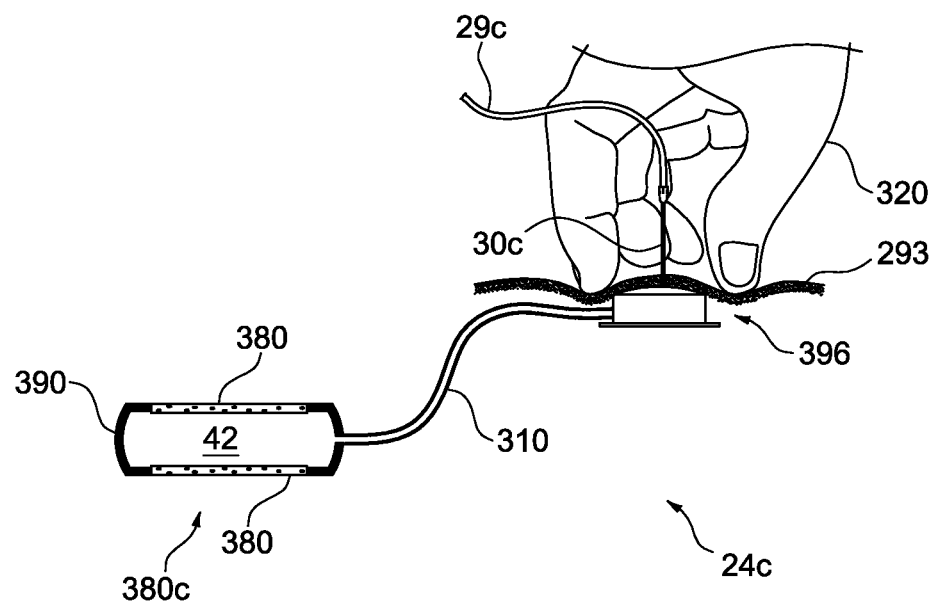

FIG. 3 schematically depicts an implantable medical device according to yet another exemplary embodiment of the current invention.

FIG. 4($a$) schematically depicts a block diagram of a gas replenishing apparatuses using a single needle according to an exemplary embodiment of the current invention.

FIG. 4($b$) schematically depicts a block diagram of a gas replenishing apparatuses using a single needle according to another exemplary embodiment of the current invention.

FIG. 4($c$) schematically depicts a block diagram of a gas replenishing apparatuses using a single needle according to yet another exemplary embodiment of the current invention.

Figure 5A:
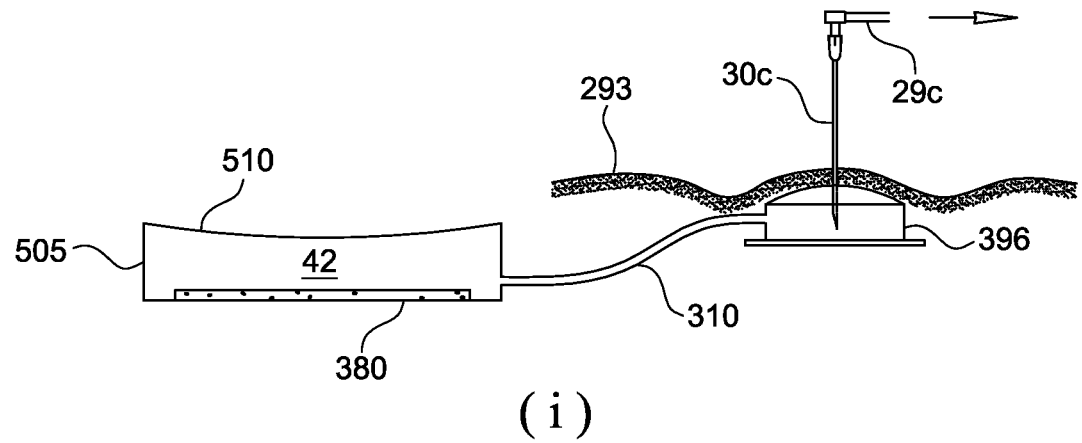
Figure 5A:
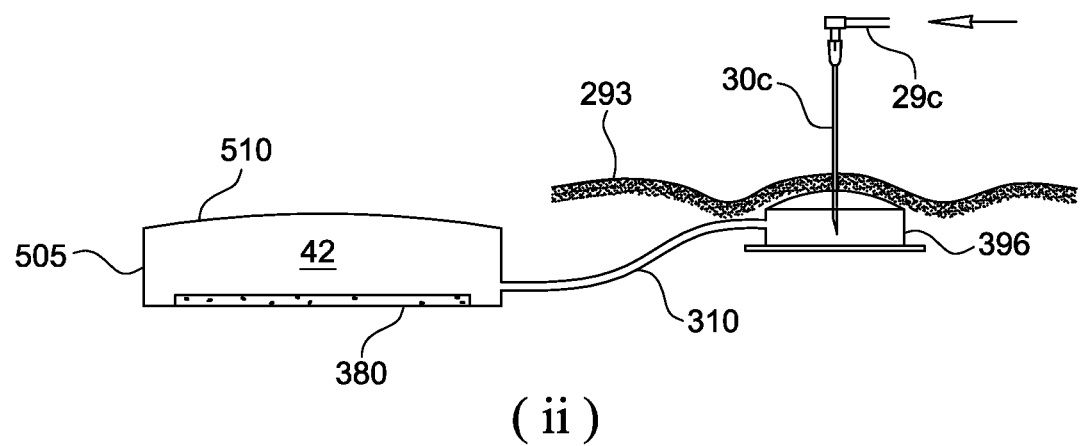

FIG. 5($a$) schematically depicts a cross section of an expandable implantable medical device according an exemplary embodiment of the current invention.

FIG. 5($b$) schematically depicts a cross section of an implantable medical device with circular gas flow according to an exemplary embodiment of the current invention.

Figure 6:
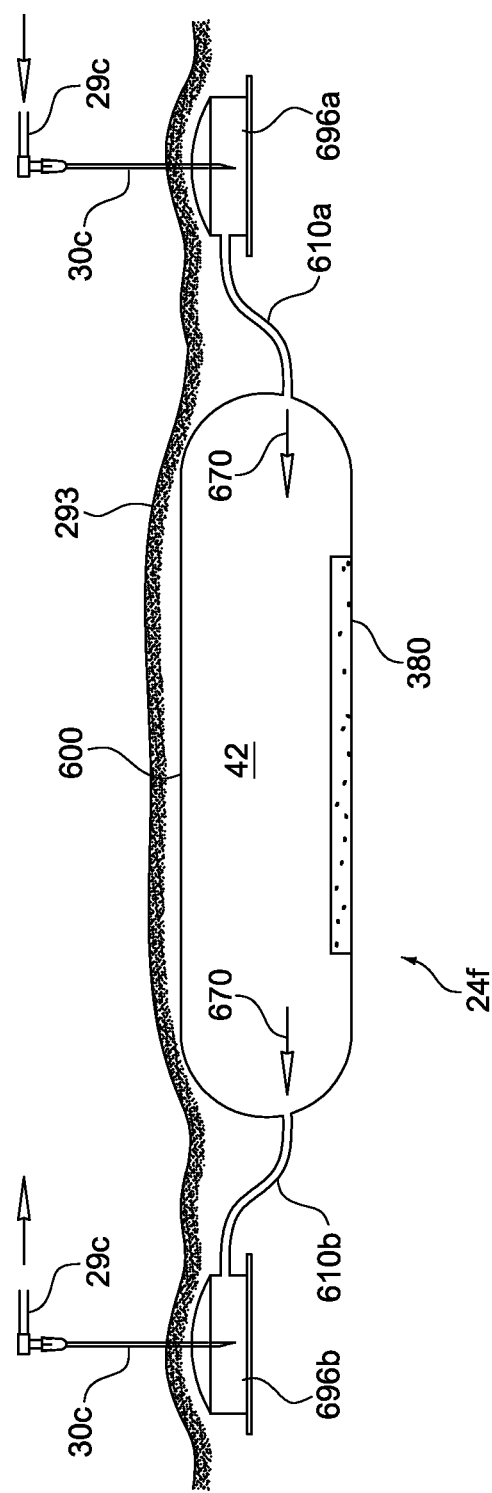

FIG. 6 schematically depicts a cross section of an implantable medical device with cross gas flow according to yet another exemplary embodiment of the current invention.

FIG. 7($a$) schematically depicts a block diagram of a gas replenishing apparatuses using an intake needle and an output needle or a dual channel needle, such as a coaxial needle, according to an exemplary embodiment of the current invention.

FIG. 7($b$) schematically depicts a block diagram of a gas replenishing apparatuses using an intake needle and an output needle or a dual channel needle, such as a coaxial needle, according to another exemplary embodiment of the current invention.

Figure 8:
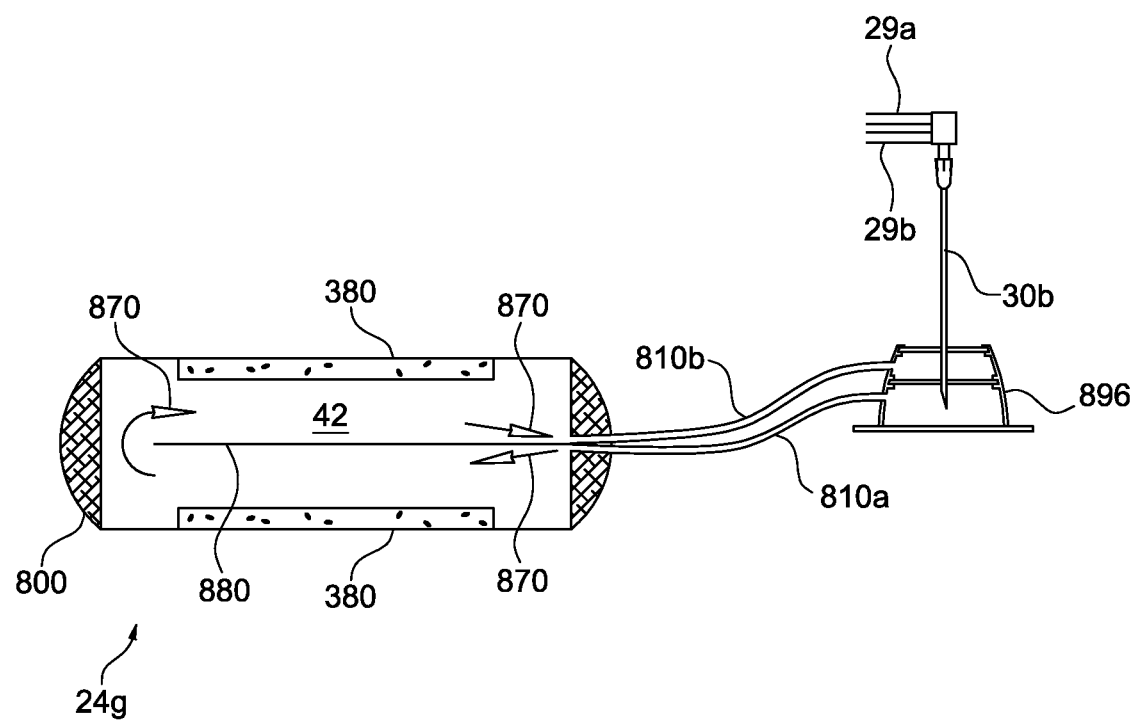

FIG. 8 schematically depicts a cross section of an implantable medical device with cross gas flow which uses a single coaxial needle according to yet another exemplary embodiment of the current invention.

Figure 9:
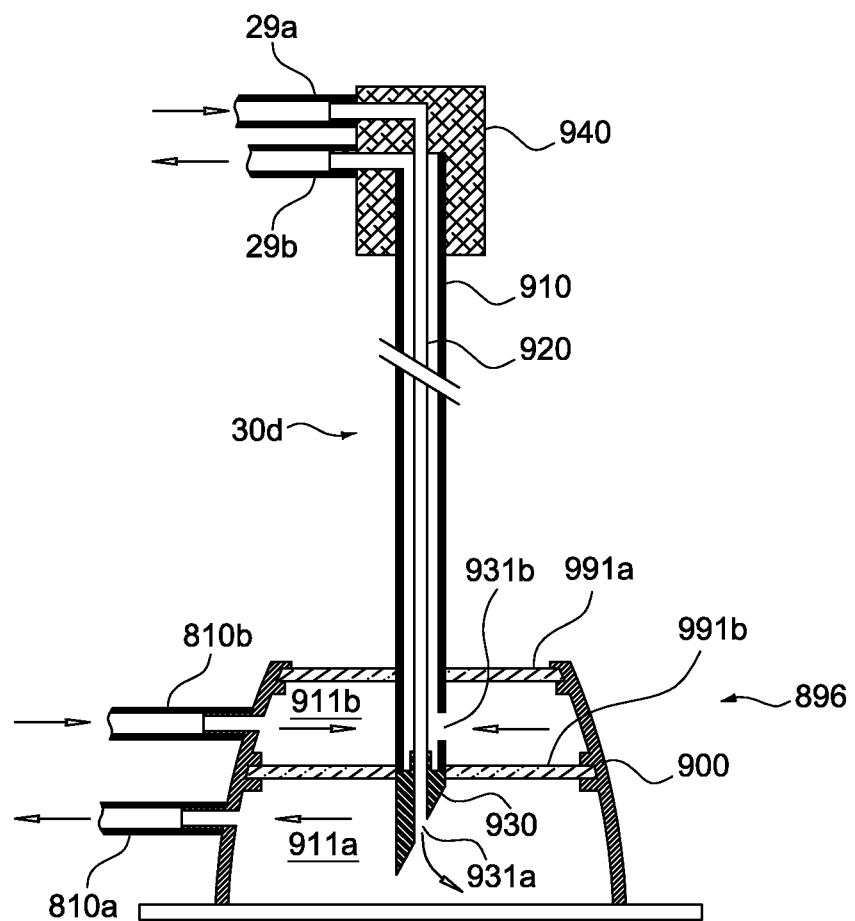

FIG. 9 schematically depicts a cross section of dual chamber port and coaxial needle according to another exemplary embodiment of the current invention.

Figure 10:
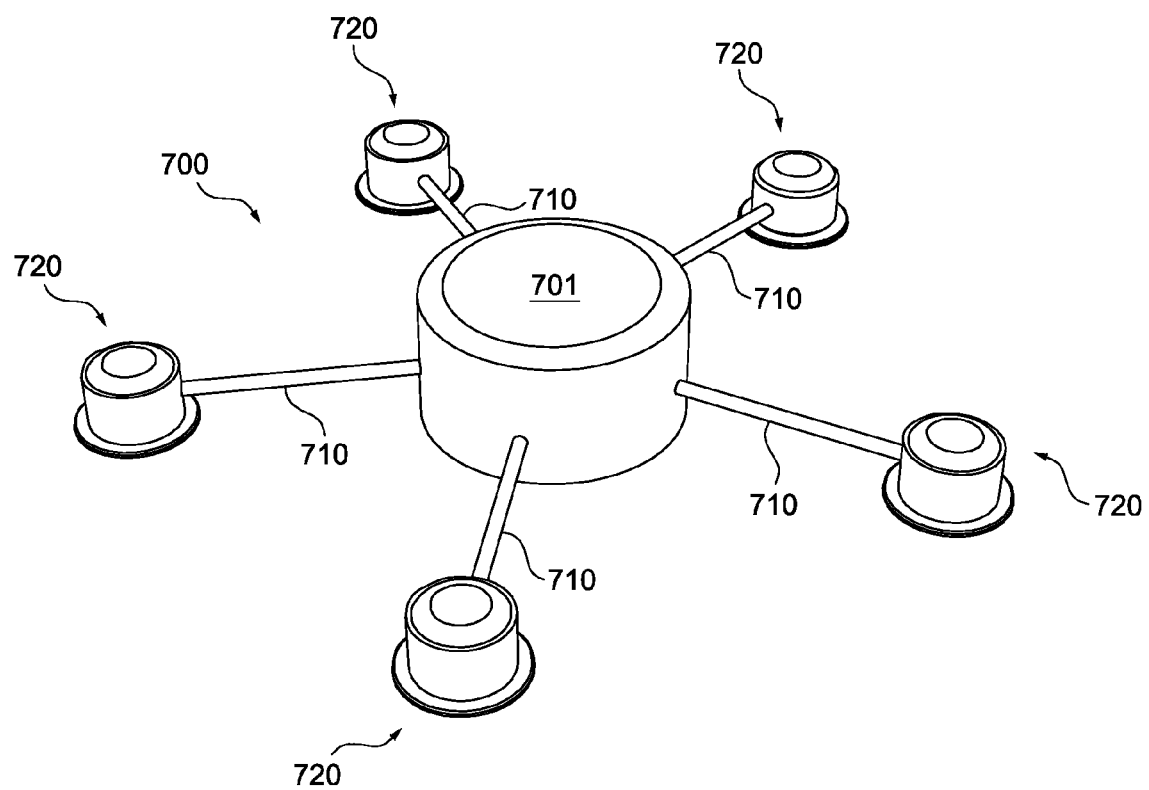

FIG. 10 schematically depicts a multi-port implantable device according to an exemplary embodiment of the current invention.

Figure 11:
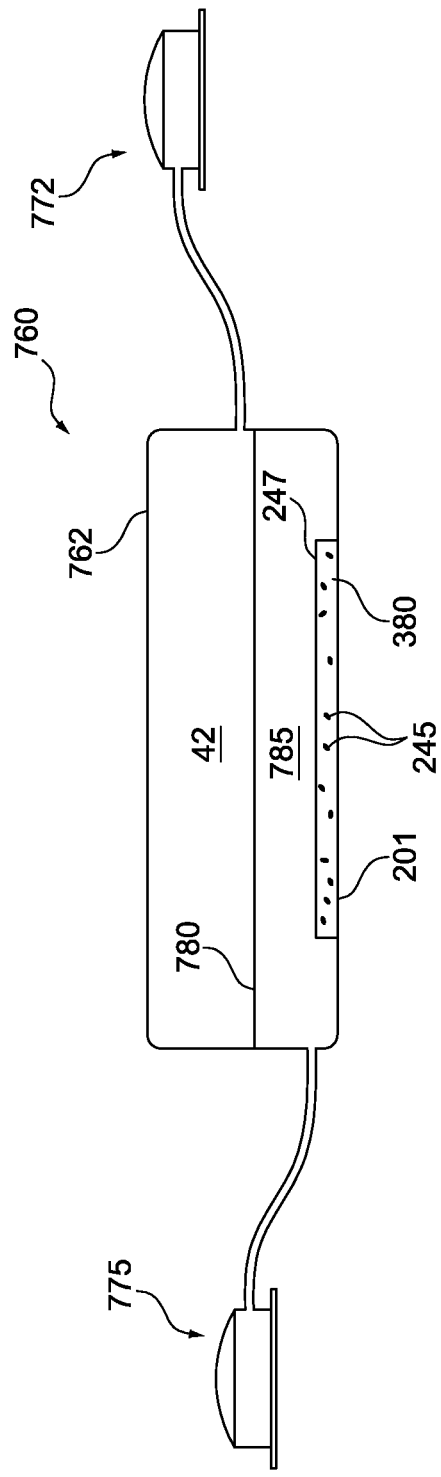

FIG. 11 schematically depicts a dual gas chamber implantable device according to an exemplary embodiment of the current invention.

DESCRIPTION OF THE PREFERRED EMBODIMENTS

The present invention relates generally to an implantable medical devices and to an apparatus and method for providing oxygen to the transplanted cells, e.g., cells in transplanted pancreatic islets within said implanted medical device.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts.

The drawings are generally not to scale. Some optional parts were drawn using dashed lines.

For clarity, non-essential elements were omitted from some of the drawings.

FIG. 1 schematically depicts a medical system 20 according to an exemplary embodiment of the current invention.

Medical system 20 comprises an implantable medical device 24, implanted in patient 22, wherein the implanted medical device 24 comprises a housing for containing transplanted cells that is designated for subcutaneous implantation into the body of a subject 22. The implanted device 24 comprises an integrated or separate filling port where the transdermal needle 30 connects to for gas filling and replenishing. The transplanted cells comprise functional cells, secreting bioactive molecules. For example, for treating diabetes, the functional cells are pancreatic islet of Langerhans cells.

The functional cells are typically disposed in a gel layer. To protect the functional cell from immune response of the patient, the functional cells are separated from the patient tissue with a semi-permeable membrane. The semi-permeable membrane is impenetrable to cells and large molecules, but allow exit of the secreted bioactive molecules from the implantable medical device 24 and allows small molecules such as glucose to enter the implantable medical device and provide nourishment for the functional cells.

Although gases such as oxygen may penetrate the membrane, it was found that functional cell do not perform properly unless additional oxygen is provided to supplement oxygen provided by diffusion from the patient tissue and blood through the semi-permeable membrane.

Thus, the implantable medical device 24, comprises an oxygen reservoir, which functions to provide oxygen to the functional cells. Oxygen supplied to the implantable medical device 24 by the oxygen replenishing apparatus 28.

The implant implanted medical device further comprises at least one subcutaneous oxygen replenishing port. Oxygen level in the gas reservoir is maintained by periodically interfacing the subcutaneous oxygen replenishing port with an oxygen replenishing apparatus 28 via at least one hollow needle 30 connected to the oxygen replenishing apparatus 28 with a hose 29. Needle 30 and optionally hose 29 are preferably single use disposables. The needle penetrates the skin and enters the subcutaneous oxygen replenishing port. Oxygen is than pumped into the gas reservoir to replenish the oxygen consumed by the functional cells. Optionally, at least some of the gas in the gas reservoir is replaced or vent during the oxygen replenishing process.

Typically, oxygen is supplied to the housing in a volume and concentration in accordance with the size of the housing and with the number of functional cells disposed therein. Additionally, the amount of oxygen delivered to the housing depends on the composition of the oxygen carriers injected into the housing. In general, the oxygen delivery interface facilitates the provision, on a consistent basis, of oxygen to the functional cells in a volume and concentration sufficient to meet the oxygen consumption rate of the functional cells over a given period of time, e.g., between 12 hours and 2 weeks.

Some details of several exemplary embodiments for the implantable medical device 24, oxygen replenishing apparatus 28, hose 29 and needle 30 will be depicted in the following figures.

Figure 2A:
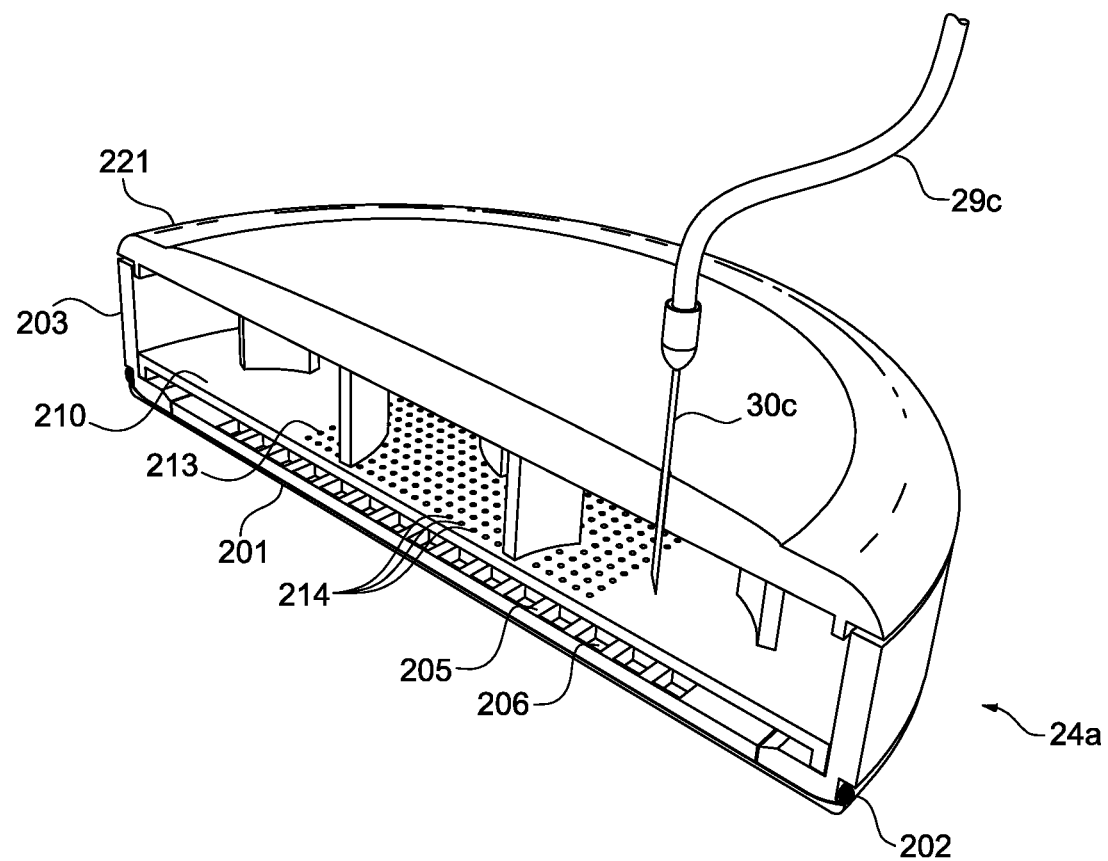

FIG. 2(a) schematically depicts an implantable medical device 24a according to an exemplary embodiment of the current invention.

Implantable medical device 24a is implanted subcutaneously, such that hypodermal needle 30c may be inserted into it through the skin. For clarity the skin and tissue were not shown in this figure.

Implantable medical device 24a comprises a housing having a solid shell 203 having a top cover 221 comprising a penetrable material, e.g., rubber, silicone, or plastic. Top cover 221 is facing the patient skin. Internal frame 210 comprises beams 21 which support top cover 221 in several locations. Bottom section of internal frame 210 comprises porous section 213 having a plurality of holes 214. The volume between top cover 211 and bottom section of internal frame 210 define a gas reservoir 42. Gas reservoir 42 may be replenished by hypodermic needle 30c which is connected to replenishing apparatus 28 (not seen in this figure) via, hose 29c. Gas from reservoir 42 defuses through holes 214 and oxygenates functional cells disposed in gel layer 206. Gel layer 206 is mechanically supported by mesh 205 and is protected from immune system of the patient by semi-permeable membrane 201 and gel. Immune Protecting membrane 201 is stretched over the bottom of solid shell 203 and held in place by elastic ring 202. Bottom section of internal frame 210 protects the gel layer against damage from needle 30c.

It should be noted that the round shape, and construction of implantable medical device 24a as depicted in FIG. 2(a) is for illustration only and other shapes and exact construction may be used within the general scope of the current invention.

Figure 2B:
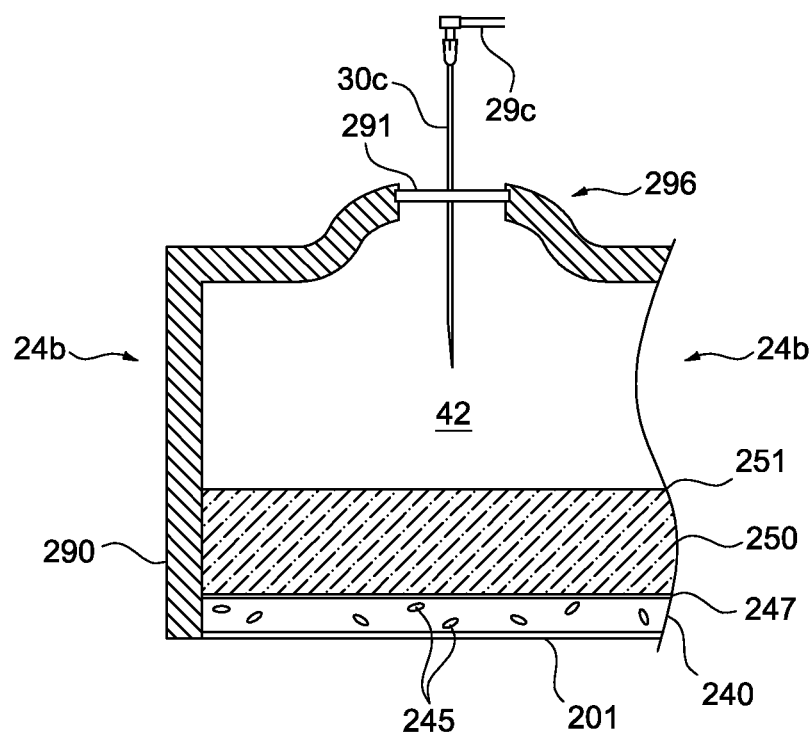

FIG. 2(b) schematically depicts an implantable medical device 24b according to another exemplary embodiment of the current invention.

Implantable medical device 24b is implanted subcutaneously; below the skin surface 293 such that hypodermal needle 30c may be inserted into it through the skin.

Implantable medical device 24b comprises a housing having a solid shell 290 having gas replenishing port 296 on its top surface. Port 296 comprises a penetrable septum 291 made of penetrable material, e.g., rubber, silicone, or plastic.

Structural rigidity of bottom surface of implantable medical device 24b is provided by a porous layer 250. Porous layer 250 may be constructed from porous metallic foam, for example high strength porous Titanium foam. Optional gas permeable membrane 251 separates gas reservoir 42 from porous layer 250. Functional cells 245 are disposed within gel layer 240 which is protected from immune system of the patient by semi-permeable membrane 201, and optionally separated from porous layer 250 by an optional second gas permeable membrane 247.

In some embodiments, gas trapped within porous layer 250 is separated from chamber 42 by gas-permeable membrane 251 and from gel layer 240 by gas-permeable membrane 247.

Functional cells 245 disposed within gel layer 240 consume nutrients diffused into the gel layer from the patient tissue through semi-permeable membrane 201. Some oxygen is also diffuses through semi-permeable membrane 201, but more oxygen is supplied to the functional cells through gas-permeable membrane 247 from gas within porous layer 250.

As oxygen is depleted in porous layer 250, its concentration in layer 250 reduces below the concentration in reservoir 42. Oxygen then diffuses from reservoir 42 into porous layer 250 through gas-permeable membrane 247. This optional construction uses porous layer 250 as a buffer gas chamber, allowing using high concentration of oxygen in reservoir 42, while maintaining lower oxygen concentration in porous layer 250. It should be noted that some types of cells may be damaged by oxidative stress caused by exposure to high concentration of oxygen. Thus, using a "buffer gas chamber" with lower oxygen concentration may prolong the life of the functional cells.

Preferably, gas in porous layer 250 comprises of gasses other than oxygen. For example, gas in porous layer 250 may comprise $CO_2$, for example due to metabolism of the functional cells. Other gases, for example nitrogen, may be present in porous layer 250 or reservoir 42. In some embodiments, oxygen concentration in porous layer is close to 20% as is in the atmosphere. Permeability of gas-permeable membrane 247 and permeability of gas-permeable membrane 240 may be selected to provide enough oxygen to the functional cells without exposing them to excessive oxygen stress.

FIG. 11 depicts an exemplary embodiment providing optional access to gas in the buffer gas chamber.

It should be noted that the shape, and construction of implantable medical device 24b as depicted in FIG. 2(b) is for illustration only and other shapes and exact construction may be used within the general scope of the current invention.

FIG. 3 schematically depicts an implantable medical device 24c according to yet another exemplary embodiment of the current invention.

Implantable medical device 24c comprises a housing 300c implanted within the patient body, for example in the abdomen, and connected to a gas replenishing port 396 with a flexible hermetic gas tube 310. Port 392 is implanted subcutaneously so it can be located by the user hand 320 through the skin 293. Similarly to replenishing port 296, port 396 comprises a penetrable septum made of penetrable material (not seen in this figure for clarity) through which needle 30c may be inserted.

Optionally, housing 300c of implantable device 24c comprises a frame 309 and bioactive surfaces 380 defining gas reservoir 42. Active surfaces 380 may be constructed in the same or similar manner as bottom surfaces of implantable devices 24a and 34b. An advantage of constructing the implantable device 24c as two separate sections: housing 300c and port 396 is the ability to have a larger volume of gas reservoir 42 than possible if the device is to be implanted subcutaneously. Additionally, larger area of active surfaces 380 comprising gel layers with functional cells is possible. By selecting the shape and size of housing 300c, the active area and volume of gas, as well as the gas volume per functional cell may be determined.

Figure 4A:
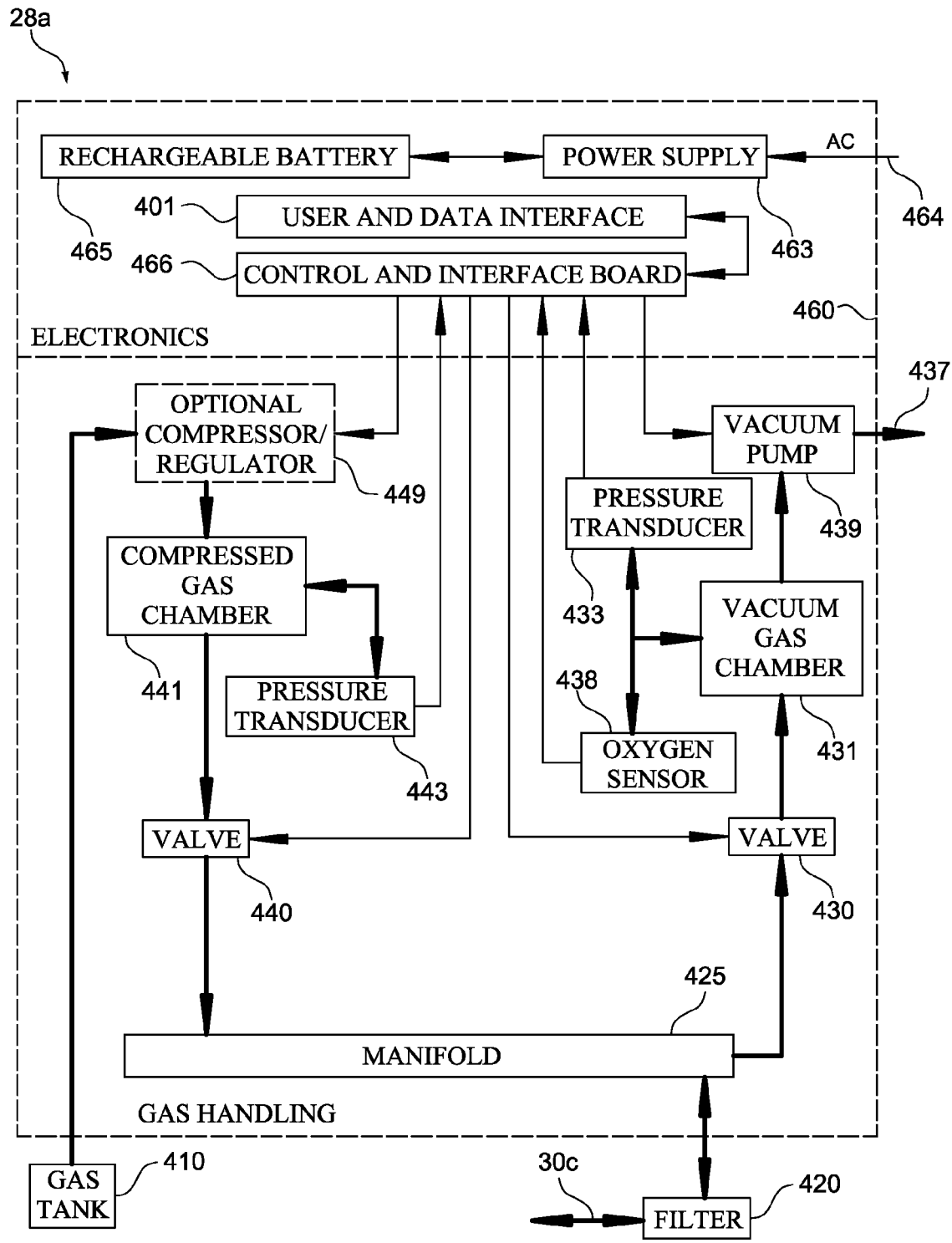
Figure 4B:
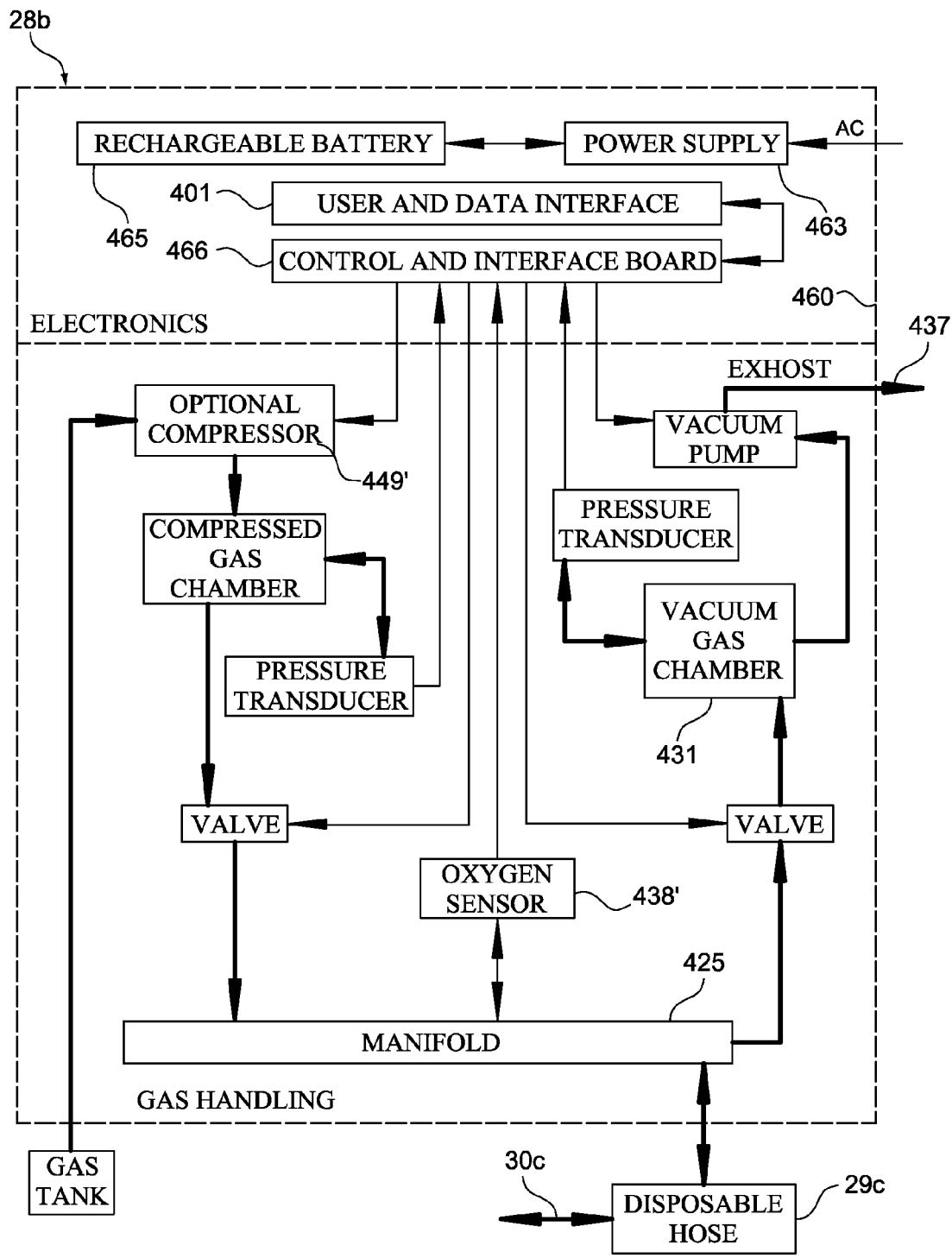
Figure 4C:
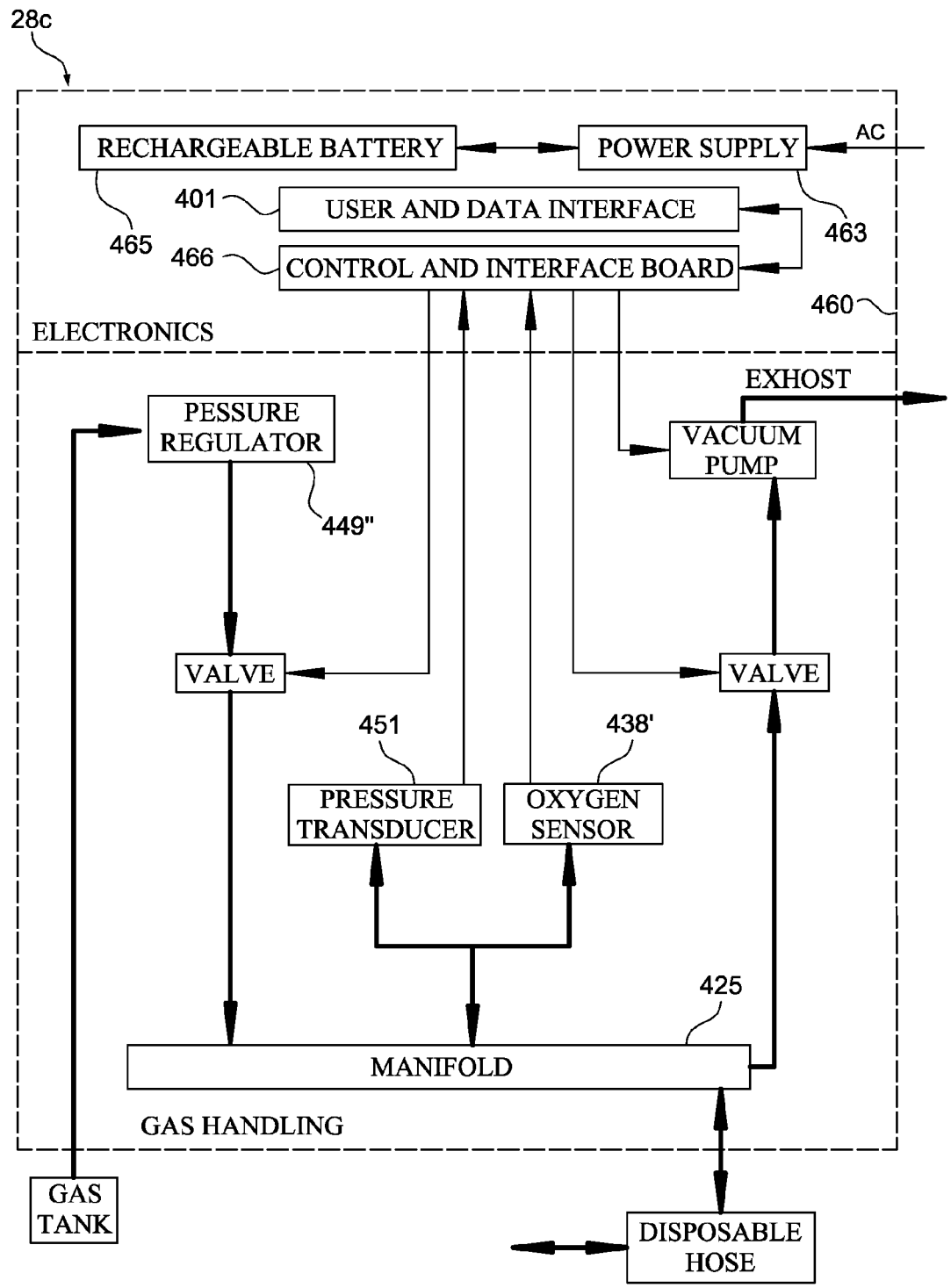

FIGS. 4(a), 4(b) and 4(c) schematically depict block diagrams of oxygen replenishing apparatuses using a single needle according to a exemplary embodiments of the current invention.

In these figures, heavy arrows denote gas conduits and light arrows denote electrical connections wherein the arrowheads indicate the direction of gas flow and the direction of electrical signals.

FIG. 4(a) schematically depicts block diagrams of oxygen replenishing apparatus using a single needle according to an exemplary embodiment of the current invention.

Oxygen replenishing apparatus 28a comprises of gas handling section 470 which is controlled by electronic section 460.

Electronic section 460 is powered by power supply 463 which may be powered by AC household power line 464. Preferably, power supply 463 may be powered by replaceable or prefer ably rechargeable battery 465. Electronic section 460 further comprises a control and interface board 466 comprising a processor, memory for storing program code, input and output devices 401 for interacting with the user, drivers for controlling gas handling actuators and signal processing inputs for receiving signals from gas sensors, and output source to drive pumps, valves and other controlling elements of the system.

User and data interface 401 may comprise user command input such as switches, or keys for activation and controlling the operation of the apparatus. Additionally, User and data interface 401 may comprise display such as indication lights or visual display for example for informing the user about the status of the apparatus (e.g. battery charge and gas supply), the progress of the gas replenishing process, results of pressure and oxygen level measurements, etc. Additionally, user and data interface 401 may comprise data communication channel for interfacing the apparatus to a computer such as a Personal Computer (PC), a remote server or a dedicated computing device for optional data logging, optional re-programming, etc. Data communication channel may be physical such as a USB port, or may be a wireless channel such as RF communication channel such as Bluetooth or Wi-Fi channel.

Oxygen replenishing apparatus 28a comprises a gas tank 410 holding a compressed oxygen or preferably gas mixture needed for oxygenation of the functional cells. Gas tank 410 may be integrated within the oxygen replenishing apparatus 28a and is periodically refilled. Alternatively tank 410 is a replaceable tank, to the apparatus and connected to the apparatus. Optionally, tank 410 is a disposable tank.

Figure 5B:
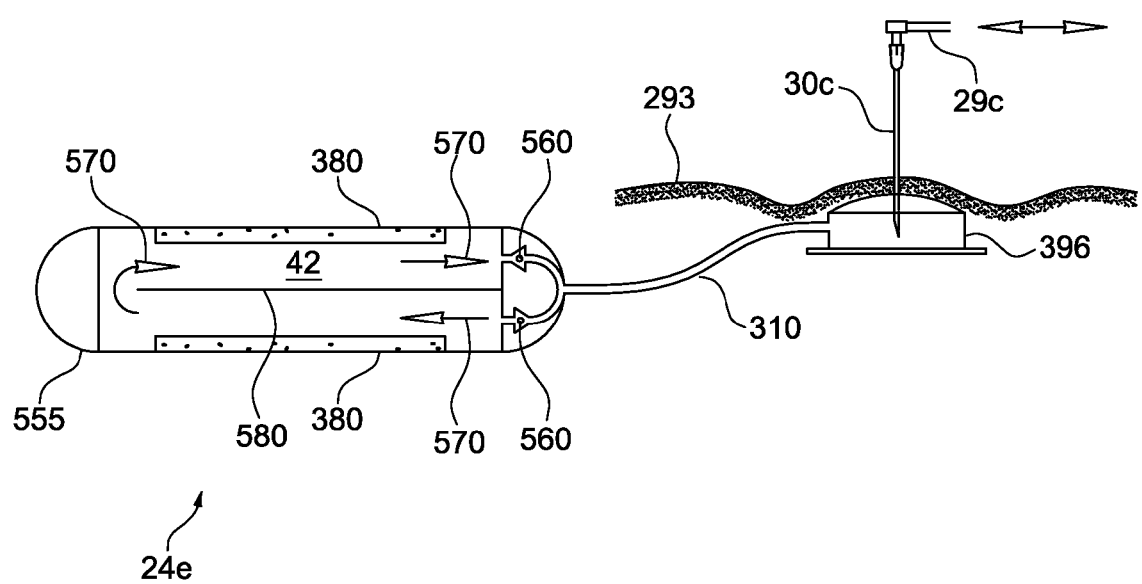

To replenish the gas in the reservoir 42 of implantable medical device 24, needle 30c is inserted into the device's reservoir as seen in FIGS. 2(a) and 2(b) or into the port as seen in FIGS. 3, 5(a) and 5(b).

Optionally a filter is located along or at one of the ends of hose 29c. Preferably, hose 29c, optional filter and needle 30c are disposable. Optionally, needle 30 is integrated with filter and hose. Alternatively, needle 30c may be separated from the hose. In this case, needle 30c may be inserted into the device or the port prior or after the hose 29 is connected.

According to an exemplary embodiment of the invention, intake valve 430 is opened, connecting the vacuum gas chamber 431 to gas reservoir 42 via needle 30c, hose 29c, and gas manifold 425. Intake pressure transducer 433 and oxygen sensor 438 monitors the pressure and oxygen concentration in reservoir 42 and based on these measures values, the control and interface board 466 determined the amount of fresh gas to be transferred from tank 410 to reservoir 42. Optionally, vacuum pump 439 is activated prior to opening intake valve 430 to evacuate vacuum gas chamber 431 to induce flow of gas from reservoir 42 into vacuum gas chamber 431.

To replenish the gas in reservoir 42, the following steps are performed and optionally repeated several times:

a) Intake valve 430 is opened, output valve 440 is closed, vacuum pump 439 is activated and some gas is pumped out of reservoir 42 and is vented through exhaust 437 while pressure transducer 433 monitors the pressure in vacuum gas chamber 431 for example to prevent too low pressure which may damage membranes in the implantable device 24, or to calculate a specific required volume. Alternatively a flow rate sensor (not shown) on the intake line, near the valve 430 is used.

b) Intake valve 430 is close, output valve 440 is opened, compressor 449 is activated and some gas is pumped into reservoir 42 while pressure transducer 443 monitors the pressure in compressed gas chamber 441 for example to prevent too high pressure which may damage membranes in the implantable device 24. Optionally, instead the compressor 449, a pressure regulator is used.

Optionally, oxygen sensor 438 monitors the intake/suction gases and terminates the replenishing amount of required gas to be replenished.

Optionally, replenishing apparatus further comprises pressure relief valves to further reduce the risk of over pressuring the implantable device.

FIG. 4(b) schematically depicts block diagrams of oxygen replenishing apparatus using a single needle 28b according to modified exemplary embodiment of the current invention. For clarity, elements identical to previous figure were not marked in this figure.

In this exemplary embodiment of the invention, oxygen sensor 483' is connected to manifold 425 instead of vacuum gas chamber 431. Oxygen sensor 438' may be used for verifying oxygen concentration of refueling gas as well as sensing oxygen concentration in pumped spent gas. As an example, in this figure, optional compressor 449' is seen where optional compressor/pressure regulator 449 is marked in FIG. 4(a).

FIG. 4(c) schematically depicts block diagrams of oxygen replenishing apparatus using a single needle 28c according to another modified exemplary embodiment of the current invention. For clarity, elements identical to previous figure were not marked in this figure.

In this exemplary embodiment of the invention, oxygen sensor 483' and pressure transducer 451 are connected to manifold 425 instead of vacuum gas chamber 431. Oxygen sensor 438' may be used for verifying oxygen concentration of refueling gas as well as sensing oxygen concentration in pumped spent gas. Similarly, pressure transducer 451 may be used for sensing gas pressure during both refueling and pumping gas from the implanted device. In this configuration, compressed gas chamber 441 and vacuum gas chamber 431 are missing. As an example, in this figure, pressure regulator 449" is seen where optional compressor/pressure regulator 449 is marked in FIG. 4(a). Note that this preferred embodiment of the invention is simpler as it requires only one pressure transducer and no chambers. Additionally, oxygen concentration may be monitored in both pumping out and providing gas to the implanted device.

Alternatively or optionally, as oxygen is consumed by functional cells in the implanted device, gas pressure is decreased in the gas reservoir. When the needle is inserted into the implanted device. Pressure transducer 451 senses the decreased pressure. Processor in 446 calculates the amount of gas needed to replenish the gas in the reservoir and activates output valve 440 accordingly. In this case, oxygen sensor 438 may be missing. Optionally, vacuum pump 439 and vacuum chamber 431 may also be missing.

FIGS. 5(a) and 5(b) schematically depicts variations of implantable medical device 24 according to exemplary embodiments of the current invention.

FIG. 5(a) schematically depicts a cross section of an expandable implantable medical device 24d according to yet another exemplary embodiment of the current invention.

In contrast to device 24c which has a substantially rigid housing, housing 505 of expandable implantable medical device 24d comprises at least one flexible wall 510, preferably comprising an elastic material such as rubber or silicon. During the pumping stage of the gas replenishing process, the flexible wall caves in as seen in FIG. 5(a)i, such as the volume or reservoir 42 decreases. During the refilling stage of the gas replenishing process, the flexible wall expand out as seen in FIG. 5(a)ii, such as the volume or reservoir 42 increases. Flexibility of wall 510 allows equalizing the pressure within the expandable implantable medical device 24d to atmospheric pressure, for example as some of the gas is consumed by the functional cells or diffuses out of the device, when barometric pressure changes or when the patient temperature changes, for example due to fever.

Additionally, the flexibility of wall 510 allows longer pumping and refilling stages with larger volume of gas in each stage and thus more efficient replenishing process.

FIG. 5(b) schematically depicts a cross section of an implantable medical device with circular gas flow 24e according to yet another exemplary embodiment of the current invention.

In order to make the gas replenishing in reservoir 42 more efficient, housing 555 of implantable medical device with circular gas flow 24e further comprises a partial divider 580 and two one way gas valves 560. During replenishing process, one way gas valves 560 forces the gas to circulate in the general direction denoted by arrows 570. This circulating gas flow prevents formation of pockets of stale gas and increases the efficiency of gas replenishing process.

FIG. 6 schematically depicts a cross section of an implantable medical device with cross gas flow 24f according to yet another exemplary embodiment of the current invention.

In order to make the gas replenishing in reservoir 42 more efficient, housing 600 of implantable medical device with cross gas flow 24f is connected to at least two ports: intake port 696a and output port 696b via intake tube 610a and output tube 610b respectively. Cross gas flow enables "flushing" the device with the required gas.

In contrast to previously shown embodiments, gas replenishing according to this exemplary embodiment of the invention is perform by flushing gas through intake hose 29a and needle 30a which is inserted in intake port 696a, through intake tube 610a into reservoir 42. Gas is vented from reservoir 42 through output gas tube 610b, output needle 30b which is inserted in output port 696b and out through output hose 29b. Gas flow is schematically depicted by arrows 670.

It should be noted that while replenishing process of implantable medical device 24a to 24e is done by repeating pumping and filling stages, replenishing gas in implantable medical device with cross gas flow 24f may be done in pumping and filling stages or in simultaneously filling new gas through intake needle 30a and venting gas through output needle 30b.

It should be noted that the relative positioning of ports 696 and housing 600 seen in FIG. 6 is for illustration only. Tubes 610 are preferably flexible and allow placing housing 600 deep in the abdomen or in another convenient location while placing ports 696 near the surface of skin 293, optionally close to each other. Gas cross flow according to this embodiment of the invention ensures efficient gas replenishing even when tubes 610 are relatively long.

Figure 7A:
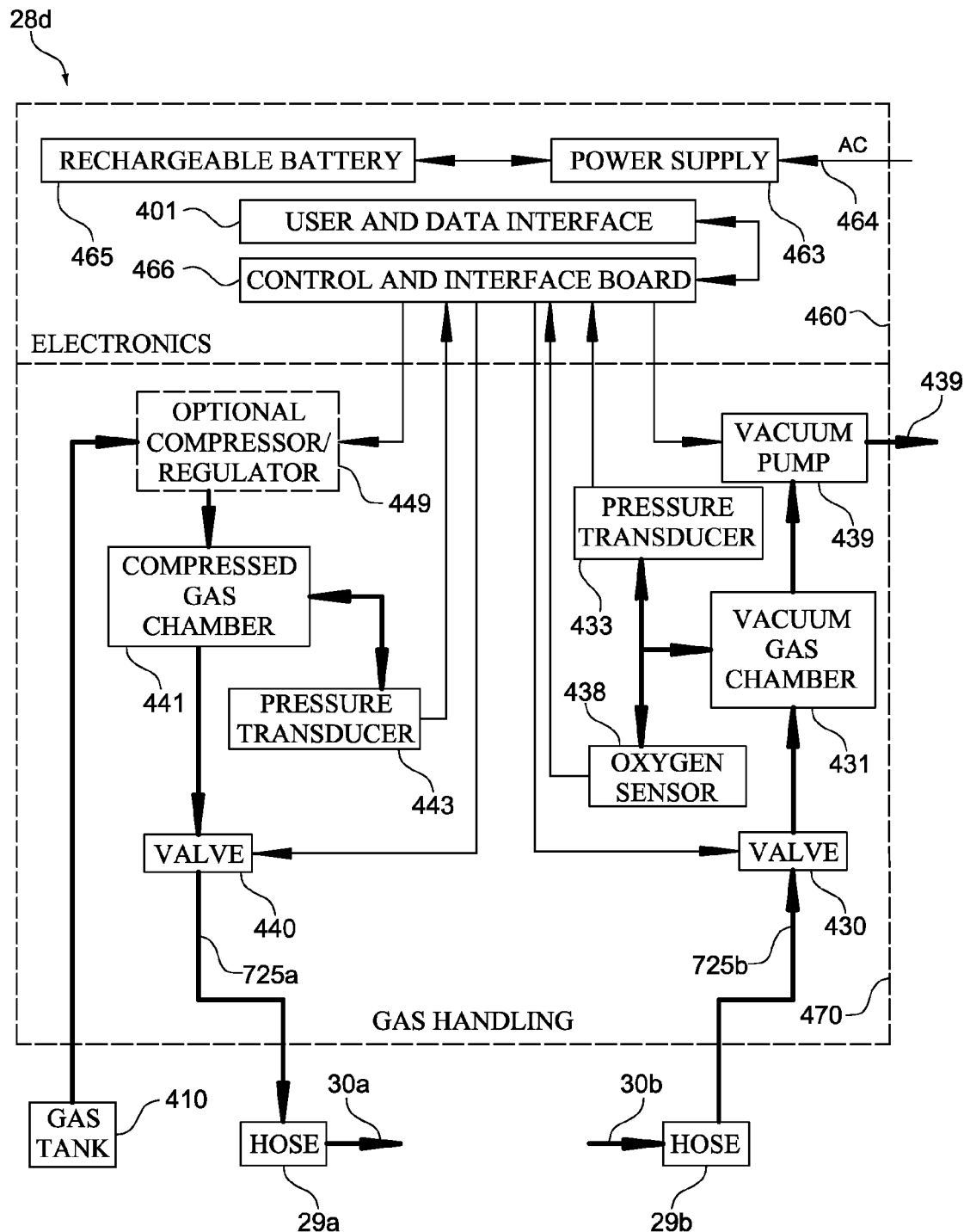
Figure 7B:
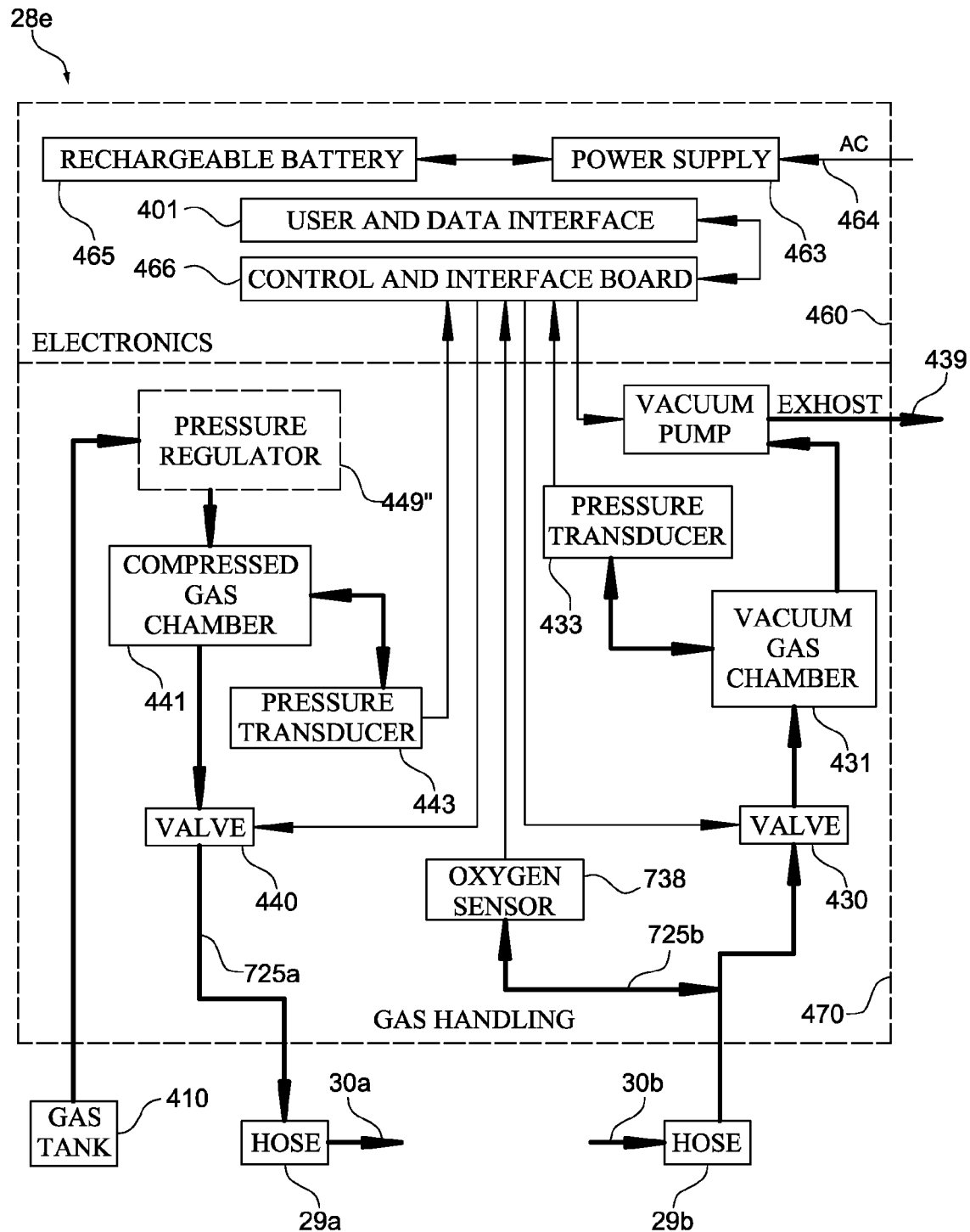

FIGS. 7(a) and 7(b) schematically depict block diagrams of oxygen replenishing apparatuses using an intake needle and an output needle according to an exemplary embodiment of the current invention. In these figures, heavy arrows denote gas conduits and light arrows denote electrical connections wherein the arrowheads indicate the direction of gas flow and the direction of electrical signals.

FIG. 7(a) schematically depicts a block diagram of a gas replenishing apparatus 28d using an intake needle 30b and an output needle 30a according to an exemplary embodiment of the current invention.

Gas/oxygen replenishing apparatus 28*d* using an intake needle and an output needle according to an exemplary embodiment of the current invention is configured to replenish oxygen in implantable medical device with cross gas flow such as device 24*f* of FIG. 6.

Oxygen replenishing apparatus 28*b* differs from apparatus 28*a* only in the fact that the gas manifold 425 is missing. Instead, intake valve 430 is connected to intake hose 29*b* via intake pipe 725*b*; and output valve 440 is connected to output hose 29*a* via output pipe 725*a*. Optionally a filter is located along or at one of the ends of hoses 29*a* and 29*b*. Preferably, hose 29*a* and 29*b*, the optional filters and needle 30*a* and 30*b* are disposable.

FIG. 7(*b*) schematically depicts a block diagram of a gas replenishing apparatus 28*e* using an intake needle and an output needle according to a modified exemplary embodiment of the current invention. For clarity, elements identical to previous figure were not marked in this figure.

Oxygen replenishing apparatus 28*e* differs from apparatus 28*d* only in the fact that oxygen sensor 738 is connected to intake pipe 725*b* instead to vacuum gas chamber 431.

To replenish the gas in the reservoir 42 of implantable medical device 24*f*, needle 30*a* is inserted into the port 696*a*, and needle 30*b* is inserted into the port 696*b* as seen in FIG. 6.

According to an exemplary embodiment of the invention, intake valve 430 is opened, connecting the vacuum gas chamber 431 to gas reservoir 42 via needle 30*b*, and hose 29*b*. Intake pressure transducer 433 and oxygen sensor 438 monitors the pressure and oxygen concentration in reservoir 42 and based on these measures values, the control and interface board 466 determined the amount of fresh gas to be transferred from tank 410 to reservoir 42. Optionally, vacuum pump 439 is activated prior to opening intake valve 430 to evacuate vacuum gas chamber 431 to induce flow of gas from reservoir 42 into vacuum gas chamber 431.

To replenish the gas in reservoir 42, the following steps are performed and optionally repeated several times:

a) Intake valve 430 is opened, output valve 440 is closed, vacuum pump 439 is activated and some gas is pumped out of reservoir 42 and is vented through exhaust 437 while pressure transducer 433 monitors the pressure in vacuum gas chamber 431 for example to prevent too low pressure which may damage membranes in the implantable device 24.

b) Intake valve 430 is close, output valve 440 is opened, compressor 449 is activated and some gas is pumped into reservoir 42 while pressure transducer 443 monitors the pressure in compressed gas chamber 441 for example to prevent too high pressure which may damage membranes in the implantable device 24. Optionally, instead the compressor 449, a pressure regulator is used.

Optionally, oxygen sensor 438 monitors the exhausted gases and terminates the replenishing process when exhaust gas contains the desired percentage of oxygen.

Alternatively, both valves 440 and 430 are opened simultaneously and both vacuum pump 439 and compressor 449 are activated. In this exemplary method of gas replenishing, gas is circulated through device 24*f*. Preferably, pressure transducer 443 monitors the in compressed gas chamber 441 for example to prevent too high pressure which may damage membranes in the implantable device 24*f*, while pressure transducer 433 monitors the pressure in vacuum gas chamber 431 for example to prevent too low pressure which may damage membranes in the implantable device 24*f* or to pressure enables calculating gas volume or flow rate. Optionally, oxygen sensor 438 monitors the exhausted gases and terminates the replenishing process when exhaust gas contains the desired percentage of oxygen.

Optionally oxygen replenishing apparatus further comprises gas flow meter or meters to monitor the amount of gas used during the replenishing process and/or rate of gas flow. Additionally or alternatively, the pump or the compressor or both are used for determining the rate of gas flow.

FIG. 8 schematically depicts a cross section of an implantable medical device with cross gas flow which uses a single coaxial needle 24*g* according to yet another exemplary embodiment of the current invention.

Gas in implantable medical device with cross gas flow which uses a single coaxial needle 24*g* is replenished by oxygen replenishing apparatus 28*b* of FIG. 7.

In order to make the gas replenishing in reservoir 42 more efficient, housing 800 of implantable medical device 24*g* comprises a partial divider 880. During replenishing process gas circulate in the general direction denoted by arrows 870.

In contrast to the embodiment depicted in FIG. 6, where two ports and two separate needles were used, in this embodiment, intake tube 810*b* and output tube 810*a* are both connected to dual chamber port 896. Details of dual chamber port 896 and coaxial needle 30*d* are given in FIG. 9.

FIG. 9 schematically depicts a cross section of dual chamber port 896 and coaxial needle 30*d* according to another exemplary embodiment of the current invention.

Dual chamber port 896 comprises a body 900 having an upper penetrable septum 291*a* and a lower penetrable septum 291*a*. Intake chamber 911*b*, defined by body 900, upper penetrable septum 291*a* and a lower penetrable septum 291*a* is opened to intake tube 810*b*. Output chamber 911*a*, defined by body 900, and a lower penetrable septum 291*a* is opened to output tube 810*a*.

Coaxial needle 30*d* comprises a central output tube 920 and outer intake tube 910. Tubes 920 and 910 are held in its distal ends by sharp tip 930 having output orifice 931*a*, and at its proximal ends by handle 940.

Output gas flow arrives from output hose 29*a*, flows through the central output tube 920, exits through output orifice 931*a* into output chamber 911*a* and flows to reservoir 42 through output tube 810.

Intake gas flow arrives into intake chamber 91*b* through intake tube 810*b*. It than enters the conduit defined between central output tube 920 and outer intake tube 910 through intake orifice 931*b* in the side of outer intake tube 910 and flows through handle 940 to intake hose 29*b*.

It should be noted that the role of upper and lower chamber, as well as inner and outer needle tubes may be reversed. Needle tubes and tip are preferably made of stainless steel.

It should be noted that using a coaxial needle 30*d* allow cross refueling of implantable device using a single needle. Thus, only one puncture of the patient's skin is needed. However, some patient may prefer two punctures with smaller diameter needles on one puncture with larger diameter.

FIG. 10 schematically depicts a multi-port implantable device 700 according to an exemplary embodiment of the current invention.

In normal operation, the implantable device is used by the patient for extended time of months or years. Frequent needle insertion at same or close sites may cause irritation of the skin. In the embodiment of FIG. 2(*a*), the needle may be inserted anywhere on the top wall 221 of implantable device 24*a*, thus enabling using different insertion sites each refueling. However, in other embodiments, such as in FIGS. 2(*b*); 3; 5(*a*); 5(*b*), 6; 8; and 9, the needle needs to be inserted into the relatively small sized port.

Multi-port implantable device 700 comprises at least one housing 701, having a gas reservoir and functional cells. Multi-port implantable device 700 further comprises at least three ports 720 connected to the housing with gas tubes 710 (five ports are seen in this exemplary embodiment). The ports are subcutaneously implanted.

It should be noted that the number of ports and their position relative to the housing and to each other may vary within the general scope of the current invention. Optionally, ports 710 are dual chamber ports such as port 896 of FIG. 9.

Optionally, ports 710 may be used with single needle refueling apparatus of FIGS. 4(*a*). 4(*b*) or 4(*c*). Additionally or alternatively, ports 710 may be used two at a time for cross gas flow replenishing using replenishing apparatuses 28*d* or 28*e* using an intake needle and an output needle depicted in FIGS. 7(*a*) and 7(*b*).

FIG. 11 schematically depicts a dual gas chamber implantable device 760 according to an exemplary embodiment of the current invention.

Implantable device 760 comprises a housing 762 comprising a reservoir 42 and a buffer gas chamber 785. Reservoir 42 and buffer gas chamber 785 are separated by gas permeable membrane 780.

Gel layer 380 with embedded functional cells/islets 245 is separated from buffer gas chamber 785 by gas permeable membrane 247.

Reservoir 42 is refueled through gas/oxygen filling port 772. Optionally, reservoir 42 is connected to a plurality of gas filling ports for cross flow replenishing or for avoiding repeated puncturing the skin at same location. Optionally, oxygen replenishing port 772 is a dual chamber port such as port 896

Optionally, gas in buffer gas chamber 785 is monitored, replaced or replenished through buffer chamber port 775. Preferably, housing 762 is connected to buffer chamber port 775 and gas replenishing port 772 via gas tubes. It should be noted that during normal use, no more than two ports are used for a refueling process simultaneously; Having an array of more than two ports enable using different combination of port pairs.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A gas replenishing apparatus for replenishing gas in a subcutaneously implanted medical device containing functional cells comprising:

at least one needle capable of penetrating the skin and connecting to the subcutaneously implanted medical device;

a gas tank holding gas for replenishing gas in said implanted device;

a gas handling sub-system capable of supplying gas from said gas tank into a gas reservoir in said implanted device;

at least one gas sensor selected from: an oxygen sensor sensing oxygen level in gas extracted from said reservoir; and a pressure transducer measuring pressure in said reservoir; and a processor for controlling said gas handling sub-system in response to reading of said at least one of said oxygen sensor and said pressure transducer, wherein said gas is capable of extracting gas from said gas reservoir; and said processor is capable of controlling said gas handling sub-system in response to sensed oxygen level in gas extracted from said gas reservoir; wherein said gas handling sub-system comprises a gas pump for extracting gas from said gas reservoir.

2. The apparatus of claim 1 and further comprising an output valve controlled by said processor, and wherein said output valve is capable of controlling amount of gas supplied from said gas tank into said gas reservoir.

3. The apparatus of claim 1 wherein said gas sensor is the pressure transducer; and wherein said processor controls said gas handling sub-system in response to sensed pressure in said gas reservoir.

4. The apparatus of claim 1 and comprising at least one pressure transducer monitoring gas pressure within said gas handling sub-system.

5. The apparatus of claim 1 wherein said at least one needle is a single needle used for both extracting gas from said gas reservoir and supplying gas from said gas tank into said gas reservoir.

6. The apparatus of claim 1 wherein said at least one needle is a single needle having a first channel and a second channel, wherein said first channel is used for extracting gas from said gas reservoir, and said second channel is used for supplying gas from said gas tank into said gas reservoir.

7. The apparatus of claim 6 wherein said first channel and said second channel are coaxial.

8. The apparatus of claim 1 wherein said at least one needle comprises a first and a second needle, wherein said first needle is used for extracting gas from said gas reservoir and said second needle is used for supplying gas from said gas tank into said gas reservoir.

9. The apparatus of claim 8 wherein said first needle and said second needle are inserted into a first and a second gas ports of the implanted medical device, respectively.

10. The apparatus of claim 1 wherein said at least one needle is capable of penetrating a gas port which is an integral part of the implanted medical device.

11. The apparatus of claim 1 wherein said at least one needle is capable of penetrating a gas port which is connected to the implanted medical device via a flexible tube.

12. A method for replenishing gas in a subcutaneously implanted medical device containing functional cells comprising:

inserting at least one needle capable of penetrating the skin and connecting to the subcutaneously implanted medical device;

connecting said at least one needle to a gas replenishing apparatus;

extracting gas from a gas reservoir in the implanted medical device into said gas replenishing apparatus;

sensing oxygen level in the gas extracted from said gas reservoir;

calculating the amount of gas needed for replenishing oxygen in said gas reservoir based on the sensed oxygen level in the extracted gas; and supplying gas from a gas tank in said gas replenishing apparatus to said gas reservoir in the implanted medical device.

13. The method of claim 12 wherein the gas in said gas tank comprises at least one gas selected from a group comprising: Oxygen, Nitrogen, Carbon dioxide; water vapor and noble gas.

14. The method of claim 12 wherein extracting gas from said gas reservoir comprises pumping the gas.

15. The method of claim 12 wherein supplying gas from the gas tank in said gas replenishing apparatus to said gas reservoir comprises opening an output valve that is controlled by a processor.

16. The method of claim 12 wherein supplying gas from the gas tank in said gas replenishing apparatus to said gas reservoir comprises operating a gas compressor controlled by a processor.

17. The method of claim 12 wherein supplying gas from the gas tank in said gas replenishing apparatus to said gas reservoir comprises reducing gas pressure in said gas tank by a pressure regulator.

18. The method of claim 12 wherein inserting at least one needle comprises inserting a single needle used for both extracting gas from said gas reservoir and supplying gas from said gas tank into said gas reservoir.

19. The method of claim 12 wherein inserting at least one needle comprises inserting a single needle having a first channel and a second channel, wherein said first channel is used for extracting gas from said gas reservoir, and said second channel is used for supplying gas from said gas tank into said gas reservoir.

20. The method of claim 12 wherein inserting at least one needle capable of penetrating the skin and connecting to a subcutaneously implanted medical device comprises inserting a first needle and a second needle into a first gas port and a second gas ports of the implanted medical device respectively, wherein said first needle is used for extracting gas from said gas reservoir, and said second needle is used for supplying gas from said gas tank into said gas reservoir.

21. The method of claim 12 wherein said at least one needle is capable of penetrating a gas port which is an integral part of the implanted medical device.

22. The method of claim 12 wherein said at least one needle is capable of penetrating a gas port which is connected to the implanted medical device via a flexible tube.

23. A method for replenishing gas in a subcutaneously implanted medical device containing functional cells comprising:

inserting at least one needle capable of penetrating skin and connecting to a subcutaneously implanted medical device;

connecting said at least one needle to a gas replenishing apparatus;

measuring a gas pressure in a gas reservoir in the implanted medical device;

calculating the amount of gas needed for replenishing oxygen in said gas reservoir based on sensed pressure in the extracted gas; and supplying gas from a gas tank in said gas replenishing apparatus to said gas reservoir in the implanted medical device.

24. A system for maintaining functional cells in medical device subcutaneously implanted in a patient body comprising:

a gas reservoir provided within the implanted medical device;

a gel layer disposed with a plurality of the functional cells, wherein said gel layer is capable of protecting the functional cells from the body immune system by a first membrane, and wherein said gel layer is capable of receiving oxygen from said gas reservoir; and at least one gas port provided to the implanted medical device that is capable of receiving replenishing gas supply;

gas replenishing apparatus located outside the patient body and capable of supplying replenishing gas to said gas reservoir through said at least one gas port wherein said gas replenishing apparatus comprising:

at least one needle capable of penetrating the skin of the patient body and connecting to the implanted medical device through said at least one gas port;

a gas tank holding gas for replenishing gas;

a gas handling sub-system capable of supplying gas from said gas tank into said gas reservoir;

at least one gas sensor selected from an oxygen sensor for sensing oxygen level in the gas; and a pressure transducer for measuring pressure in said gas reservoir; and a processor capable of controlling said gas handling sub-system in response to reading of said at least one of said oxygen sensor and said pressure transducer.

25. The system of claim 24 wherein said gas handling sub-system is capable of extracting gas from said gas reservoir and said processor is capable of controlling said gas handling sub-system in response to reading oxygen level sensed in the gas.

26. The system of claim 24 and further comprising at least one hose connecting said at least one needle to said gas replenishing apparatus.

27. The system of claim 26 wherein said at least one hose is flexible.

28. The system of claim 24 wherein said implanted device comprises at least a first and a second gas ports, both connected to said gas reservoir.

29. The system of claim 28 wherein said gas replenishing apparatus comprises a first and a second needle inserted into said first and a second gas ports of said implanted device respectively, wherein said first needle is used for extracting gas from said gas reservoir, and said second needle is used for supplying gas from said gas tank into said gas reservoir.

30. The system of claim 24 wherein the implanted medical device further comprises a buffer gas chamber located between said gel layer with functional cells and said gas reservoir and wherein said gas reservoir is separated from said gel layer by a second membrane.

31. The system of claim 30 wherein the implanted medical device comprises at least a first and a second gas port, and wherein said first gas port is connected to said gas reservoir, and said second port is connected to said buffer gas chamber.

32. The system of claim 30 wherein said gas replenishing apparatus comprises at least a first and a second needle inserted into said at least one gas port wherein said first needle is used for extracting gas from said buffer gas chamber, and said second needle is used for supplying gas from said gas tank into said gas reservoir.

33. A gas replenishing apparatus for replenishing gas in a subcutaneously implanted medical device containing functional cells comprising:

at least one needle capable of penetrating the skin and connecting to a subcutaneously implanted medical device;

a gas tank holding gas for replenishing gas in the implanted medical device;

a gas handling sub-system capable of supplying a predetermined amount of gas from said gas tank into a gas reservoir in the implanted medical device and further comprising a timer, wherein said timer is capable of measuring the time elapsed since last gas replenishing, and wherein said predetermined amount of gas is selected according to the elapsed time.

34. The apparatus of claim 33 wherein said predetermined amount of gas is fixed and wherein time between consecutive gas replenishing is substantially fixed.

* * * * *